(12) United States Patent
Neuenschwander

(10) Patent No.: US 8,382,734 B1
(45) Date of Patent: Feb. 26, 2013

(54) ADULT DIAPER SYSTEM

(76) Inventor: Lois Jean Neuenschwander, Oneco, FL (US)

( * ) Notice: Subject to any disclaimer, the term of this patent is extended or adjusted under 35 U.S.C. 154(b) by 475 days.

(21) Appl. No.: 12/655,853

(22) Filed: Jan. 8, 2010

(51) Int. Cl.
*A61F 13/15* (2006.01)
(52) U.S. Cl. ....... 604/385.19; 604/385.11; 604/385.101; 604/385.14; 604/385.09
(58) Field of Classification Search .............. 604/385.19, 604/385.11, 385.101, 385.14, 385.09
See application file for complete search history.

(56) References Cited

U.S. PATENT DOCUMENTS 4,834,737 A * 5/1989 Khan ...................... 604/385.14

* cited by examiner

*Primary Examiner* — Jacqueline F. Stephens
(74) *Attorney, Agent, or Firm* — Dorothy S. Morse

(57) ABSTRACT

A primary component is formed of a flexible sheet with a periphery and a central opening, an exterior recipient surface, and an interior surface with an adhesive for removably coupling to a user with the central opening positionable over the anus of the user. A container has a chamber and an opening for receiving and collecting fecal matter. An intermediate member has a separable fastener removably coupling the container with the primary component.

12 Claims, 3 Drawing Sheets

ADULT DIAPER SYSTEM

BACKGROUND OF THE INVENTION

Field of the Invention

The present invention relates to an adult diaper system and more particularly pertains to facilitating the collection and disposal of fecal matter, in a sanitary, convenient and economical manner.

SUMMARY OF THE INVENTION

In view of the foregoing disadvantages inherent in the known types of diaper systems of known designs and configurations now present in the prior art, the present invention provides an improved adult diaper system. As such, the general purpose of the present invention, which will be described subsequently in greater detail, is to provide a new and improved adult diaper system and method which has all the advantages of the prior art and none of the disadvantages.

To attain this, the present invention essentially comprises an adult diaper system. First provided is a primary component. The primary component is formed of a flexible sheet with an oval periphery and a central circular opening. The primary component has an exterior recipient surface. The primary component also has an interior surface with an adhesive. The adhesive is for removably coupling the primary component to a user with the circular opening located over an anus of the user.

Next provided is a diaper. The diaper has an imperforate exterior layer. The diaper also has an interior layer formed with an aperture. The diaper, when worn by the user, is positioned with the aperture adjacent to the opening of the primary component. The exterior layer is fabricated of a moisture absorbent material with a moisture impervious outside coating. The interior layer is fabricated of a moisture absorbent material with a moisture impervious outside coating. A chamber is formed in the diaper between the interior and exterior layers for receiving and collecting fecal matter.

An intermediate member is next provided for coupling the primary component and the diaper. The intermediate member has a short tubular portion removably positioned through the aperture of the diaper. The intermediate member has a circular outer portion positionable on the outside coating of the interior layer of the diaper. The outer portion has a layer of adhesive in an oval configuration corresponding in size and shape to the primary component with a circular passageway corresponding to the opening in the primary component. A separable peel sheet is provided over the adhesive. The separable peel sheet is removed prior to use. The intermediate member has a circular inner portion positionable within the chamber of the diaper. The inner portion has a surface with a pile type fastener for removable coupling of the intermediate member to the interior layer of the diaper.

Lastly, a plurality of radially extending ribs is provided. The ribs are attached to and emanate from the inner portion of the intermediate member. The ribs have inner ends adjacent to the tubular portion of the intermediate member. The tubes have outer ends remote from the tubular portion of the intermediate member. The ribs are adapted to hold the inner portion and the chamber in an extended operative open orientation for receiving and holding fecal matter within the chamber.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved adult diaper system which has all of the advantages of the prior art diaper systems of known designs and configurations and none of the disadvantages.

It is another object of the present invention to provide a new and improved adult diaper system which may be easily and efficiently manufactured and marketed.

It is further object of the present invention to provide a new and improved adult diaper system which is of durable and reliable constructions.

An even further object of the present invention is to provide a new and improved adult diaper system which is susceptible of a low cost of manufacture with regard to both materials and labor, and which accordingly is then susceptible of low prices of sale to the consuming public, thereby making such adult diaper system economically available to the buying public.

Even still another object of the present invention is to provide an adult diaper system for facilitating the collection and disposal of fecal matter, in a sanitary, convenient and economical manner.

Lastly, it is an object of the present invention to provide a new and improved adult diaper system. A primary component is formed of a flexible sheet with a periphery and a central opening, an exterior recipient surface, and an interior surface with an adhesive for removably coupling to a user with the central opening positionable over the anus of the user. A container has a chamber and an opening for receiving and collecting fecal matter. An intermediate member has a separable fastener removably coupling the container with the primary component.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
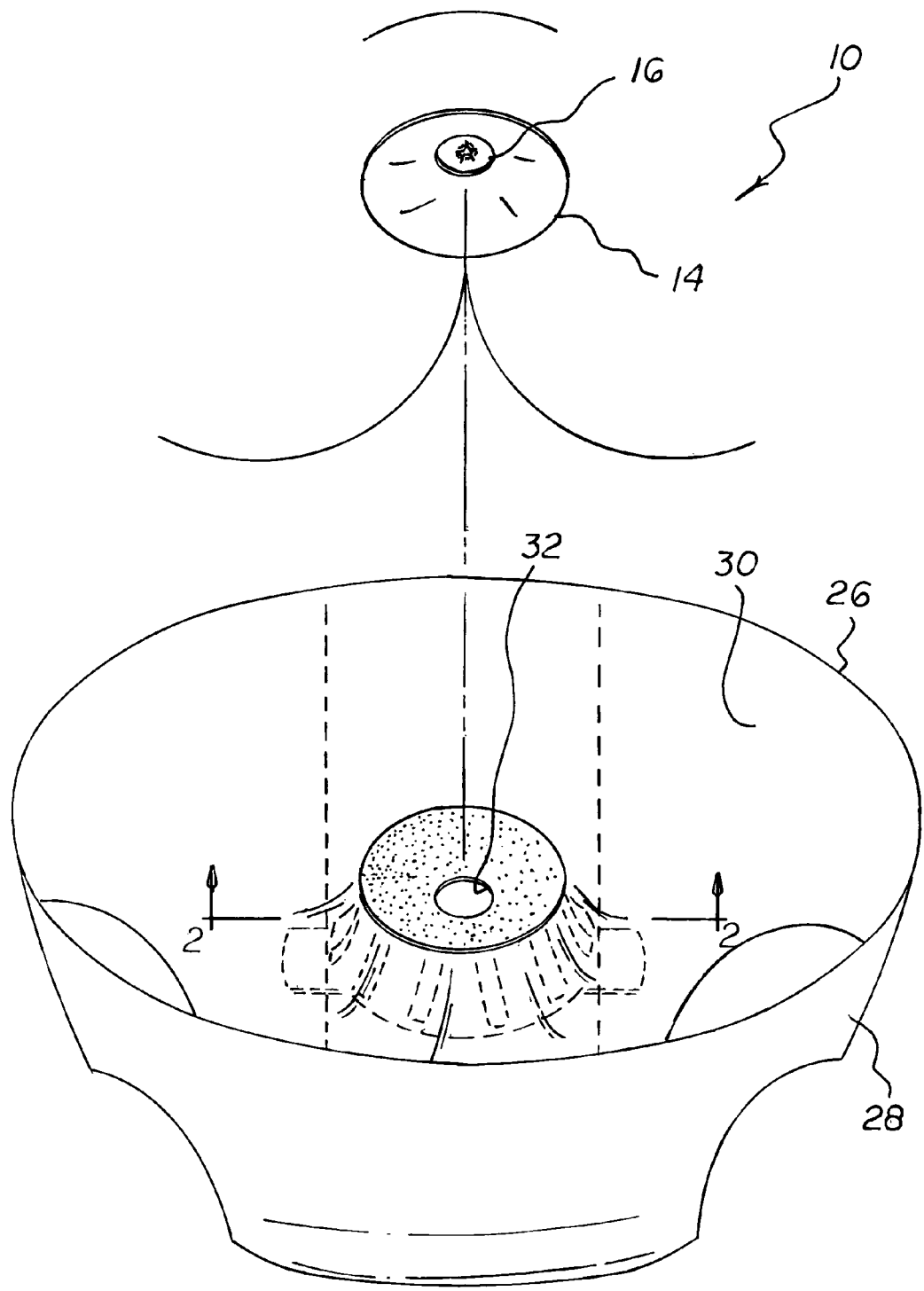
FIG. 1 is an exploded perspective illustration of an adult diaper system constructed in accordance with the principles of the present invention.
Figure 2:
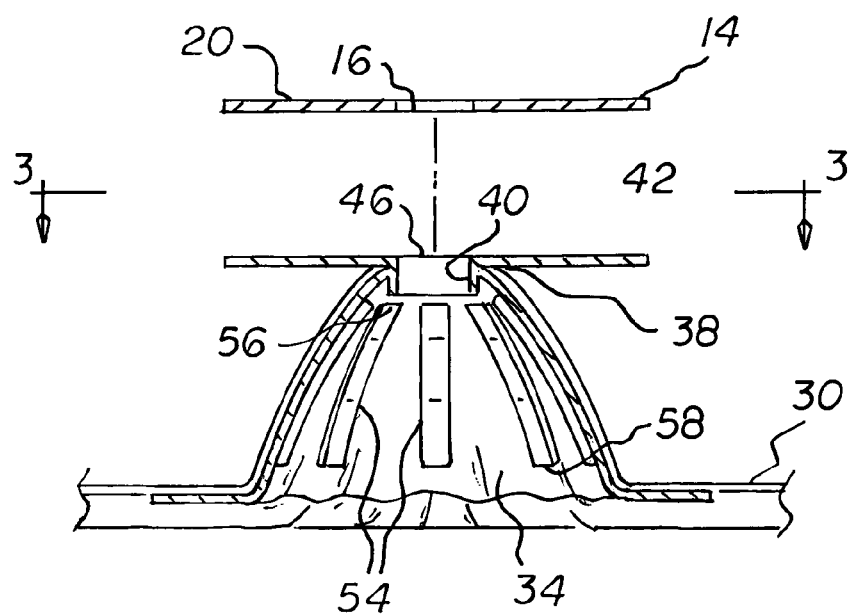
FIG. 2 is a cross sectional view of the primary component shown in FIG. 1.
Figure 3:
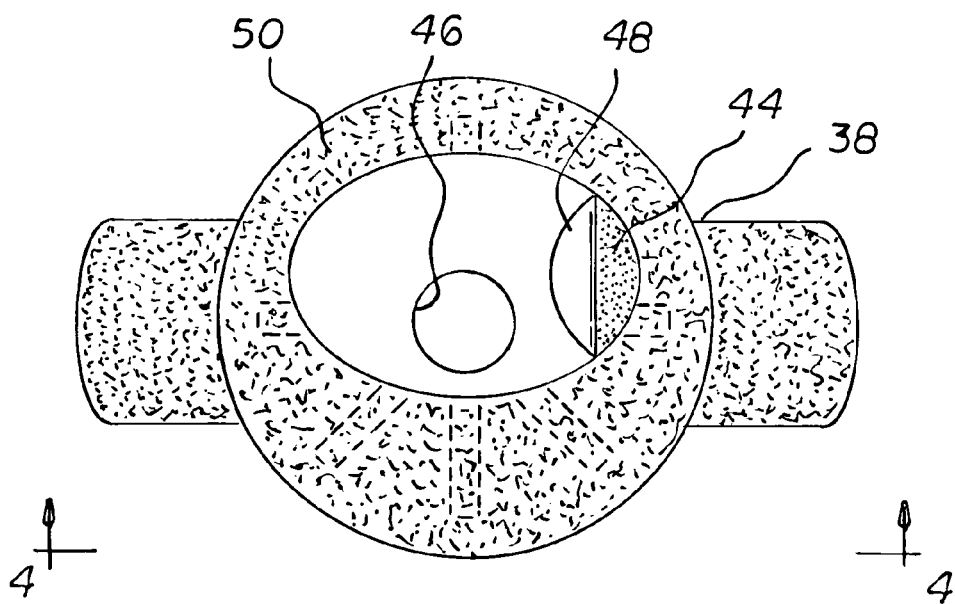
FIG. 3 is a cross sectional view taken along line 3-3 of FIG. 2.
Figure 4:
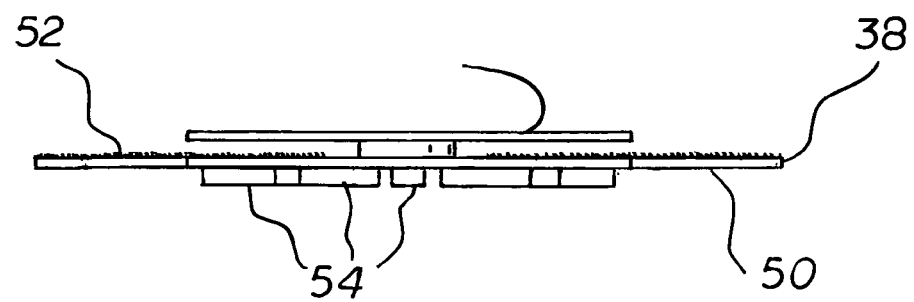
FIG. 4 is a cross sectional view taken along line 4-4 of FIG. 3.

With reference now to the drawings, and in particular to FIG. 1 thereof, the preferred embodiment of the new and improved adult diaper system embodying the principles and concepts of the present invention and generally designated by the reference numeral 10 will be described.

The present invention, the adult diaper system 10 is comprised of a plurality of components. Such components in their broadest context include a primary component, a container and an intermediate member. Such components are individually configured and correlated with respect to each other so as to attain the desired objective.

First provided is a primary component 14. The primary component is formed of a flexible sheet with an oval periphery and a central circular opening 16. As can be seen in FIG. 1, the central circular opening can be offset toward one side of the periphery. The primary component also has an interior surface 20 with an adhesive 22. The adhesive is for removably coupling the primary component to a user with the circular opening located over the anus of the user.

Next provided is a diaper 26. The diaper has an imperforate exterior layer 28. The diaper also has an interior layer 30 formed with an aperture 32. The diaper, when worn by the user, is positioned with the aperture adjacent to the opening of the primary component. The exterior layer is fabricated of a moisture absorbent material with a moisture impervious outside coating. The interior layer is fabricated of a moisture absorbent material with a moisture impervious outside coating. A chamber 34 is formed in the diaper between the interior and exterior layers for receiving and collecting fecal matter.

An intermediate member 38 is next provided for coupling the primary component and the diaper. The intermediate member has a short tubular portion 40 removably positioned through the aperture of the diaper. The intermediate member has a circular outer portion 42 positionable on the outside coating of the interior layer of the diaper. The outer portion has a layer of adhesive 44 in an oval configuration corresponding in size and shape to the primary component with a circular passageway 46 corresponding to the opening in the primary component. Other coupling materials between the primary member and intermediate member could readily be utilized. A separable peel sheet 48 is provided over the adhesive. The separable peel sheet is removed prior to use. The intermediate member has a circular inner portion 50 positionable within the chamber of the diaper. The inner portion has a surface with a pile type fastener 52 for removable coupling of the intermediate member to the interior layer of the diaper. The surface of the inner portion is preferably circular and preferably with tabs. A wide variety of other shapes could readily be utilized.

Lastly, a plurality of radially extending ribs 54 is provided. The ribs are attached to and emanate from the inner portion of the intermediate member. The ribs have inner ends 56 adjacent to the tubular portion of the intermediate member. The tubes have outer ends 58 remote from the tubular portion of the intermediate member. The ribs are adapted to hold the inner portion and the chamber in an extended operative open orientation for receiving and holding fecal matter within the chamber.

Figure 5:
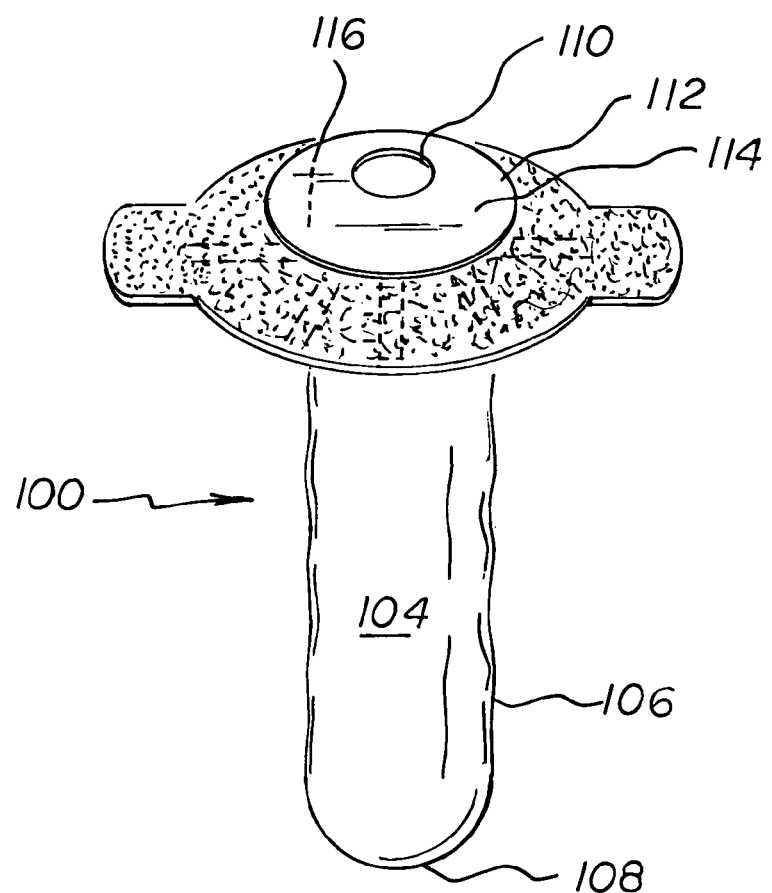
FIG. 5 is a perspective illustration an alternate embodiment of the invention.

Reference is now made to the alternate embodiment of the system 100 as illustrated in FIG. 5. In this embodiment, the container 104 is a cylindrical member fabricated of a moisture impervious material and formed of a continuous side wall 106 with a closed bottom 108 and an open top 110. In this embodiment, the intermediate member is an oval disk 112. The oval disk has a first surface 114 attached to the container adjacent to the open top. The oval disk also has a second surface with an adhesive 116 adapted to releasably couple the container to the primary component.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. An adult diaper system comprising, in combination:
   a primary component formed of a flexible sheet with a periphery and a central opening, the primary component having an exterior recipient surface, the primary component having an interior surface with an adhesive for removably coupling to a user with a central opening positionable over the anus of a user;
   a fecal receiving and collecting container with an interior layer and an exterior layer, said interior and exterior layers each fabricated from moisture absorbent material having a moisture impervious outside coating, said interior layer and said exterior layer positioned so that said moisture absorbent materials face one another and said moisture impervious outside coatings are located remotely from one another, said interior layer also centrally separable from said exterior layer to form a chamber therebetween, and said interior layer having an opening configured for receiving fecal matter from the user and collection thereof in said chamber; and
   an intermediate member secured to said primary component and said container, said intermediate member having a short tubular portion with an outer portion and a circular inner portion depending therefrom, said short tubular portion removably positionable through said opening in said interior layer of said container, said outer portion having one side with a separable fastener corresponding in size and shape to said exterior recipient surface of said primary component and its opposed side positionable on said moisture impervious outside coating of said interior layer of said container, said outer portion also having a circular passageway corresponding to said opening in said primary component, and said circular inner portion positionable within said chamber and having a pile type fastener for removable coupling of said intermediate member to said interior layer of said container, wherein when said primary component is coupled to a user, said short tubular portion of said intermediate member is positioned through said opening in said interior layer of said container and said circular inner portion of said intermediate member is positioned within said chamber, coupling of said separable fastener on said outer portion of said intermediate member with said exterior recipient surface of said primary component causes central separation of said interior layer of said container from said exterior layer of said container and formation of said chamber used for receipt and collection of fecal matter.

2. The system as set forth in claim 1 wherein said circular inner portion of said intermediate member further comprises at least one tab.

3. The system as set forth in claim 1 wherein said container is a cylindrical member fabricated of a moisture impervious material and formed of a continuous sidewall with a closed bottom and an open top and wherein said intermediate member is an oval disc having a first surface attached to said container adjacent to said open top and a second surface with an adhesive adapted to releasably couple said container to said primary component.

4. The system as set forth in claim 1 wherein said short tubular portion further comprises a plurality of ribs adapted to hold said chamber in an extended operative open configuration for receipt and collection of fecal matter.

5. The system as set forth in claim 1 wherein said periphery of said primary component is oval.

6. The system as set forth in claim 5 wherein said central opening of said primary component is offset toward one side of said periphery.

7. The system as set forth in claim 1 wherein said outer portion of said intermediate member has a circular configuration.

8. The system as set forth in claim 1 wherein said central opening of said primary component is offset toward one side of said periphery.

9. The system as set forth in claim 1 wherein said separable fastener on said outer portion of said intermediate member is adhesive.

10. The system as set forth in claim 9 further comprising a separable peel sheet over said adhesive for removal prior to use.

11. An adult diaper system comprising, in combination:
a primary component formed of a flexible sheet with a periphery and a central opening, said primary component having an exterior recipient surface and an interior surface with an adhesive for removably coupling to a user, said primary component also having a central opening positionable over the anus of a user;
a diaper with an interior layer and an exterior layer, said interior layer centrally separable from said exterior layer to form a chamber therebetween, said interior layer having an opening configured for receiving fecal matter from the user and collection thereof in said chamber;
an intermediate member with a separable fastener removably coupling said container with said primary component that causes said coupling to separate said interior layer from said exterior layer to form said chamber, said intermediate member having a short tubular portion, a circular outer portion positionable on the interior layer of the diaper, said outer portion having a layer of adhesive in an oval configuration corresponding in size and shape to said primary component with a circular passageway corresponding to said opening in said primary component, a separable peel sheet over said adhesive for removal prior to use, said intermediate member also having a circular inner portion positionable within said chamber of said diaper, said inner portion having a surface with a pile type fastener for removable coupling to said interior layer of said diaper; and a plurality of radial extending ribs attached to and emanating from said inner portion of said intermediate member, said Ribs having inner ends adjacent to said tubular portion, said ribs having outer ends remote from said tubular portion, said ribs adapted to hold said inner portion and said chamber in an extended operative orientation for receiving and holding fecal matter therein.

12. An adult diaper system for facilitating the collection and disposal of fecal matter, the system comprising, in combination:
a primary component formed of a flexible sheet with an oval periphery and a central circular opening, the primary component having an exterior recipient surface, the primary component having an interior surface with an adhesive for removably coupling the primary component having an interior surface with an adhesive for removably coupling the primary component to a user with the circular opening located over the anus of the user;
a diaper having an imperforate exterior layer and an interior layer formed with an aperture, the diaper when worn by a user being positioned with the aperture adjacent to the opening of the primary component, the exterior layer being fabricated of a moisture absorbent material with a moisture impervious outside coating, the interior layer being fabricated of a moisture absorbent material with a moisture impervious outside coating, a chamber formed in the diaper formed between the interior and exterior layers for receiving and collecting fecal matter;
an intermediate member coupling the primary component in the diaper, the intermediate member having a short tubular portion removably positioned through the aperture of the diaper, the intermediate member having a circular outer portion positionable on the outside coating of the interior layer of the diaper, the outer portion having a layer of adhesive in an oval configuration corresponding in size and shape to the primary component with a circular passageway corresponding to the opening in the primary component, a separable peel sheet over the adhesive for removal prior to use, the intermediate member having a circular portion positionable within the chamber of the diaper, the inner portion having a surface with a pile type fastener for removable coupling the intermediate member to the interior layer of the diaper; and
a plurality of radially extending ribs attached to and emanating from the inner portion of the intermediate member, the ribs having inner ends adjacent to the tubular portion of the intermediate member, the ribs having outer ends remote from the tubular portion of the intermediate member, the ribs adapted to hold the inner portion and the chamber in an extended operative open orientation for receiving and holding fecal matter within the chamber.

* * * * *